(12) United States Patent
Bessette et al.

(10) Patent No.: US 7,008,649 B2
(45) Date of Patent: Mar. 7, 2006

(54) CANCER TREATMENT COMPOSITION AND METHOD USING NATURAL PLANT ESSENTIAL OILS WITH SIGNAL TRANSDUCTION MODULATORS

(75) Inventors: Steven M. Bessette, Brentwood, TN (US); Essam E. Enan, Franklin, TN (US)

(73) Assignee: Ecosmart Techonlogies, Inc., Franklin, TN (US)

( * ) Notice: Subject to any disclaimer, the term of this patent is extended or adjusted under 35 U.S.C. 154(b) by 0 days.

(21) Appl. No.: 10/770,386

(22) Filed: Feb. 4, 2004

(65) Prior Publication Data

US 2004/0156922 A1 Aug. 12, 2004

Related U.S. Application Data

(62) Division of application No. 09/455,543, filed on Dec. 7, 1999, now abandoned.

(60) Provisional application No. 60/111,271, filed on Dec. 7, 1998.

(51) Int. Cl.
  *A61K 35/78* (2006.01)
(52) U.S. Cl. ..................................................... 424/725
(58) Field of Classification Search ............. 424/195.1, 424/725
  See application file for complete search history.

(56) References Cited

U.S. PATENT DOCUMENTS

| | | | |
|---|---|---|---|
| 4,261,989 A | | 4/1981 | Sasaki et al. |
| 4,751,224 A | * | 6/1988 | Agarwal et al. ............. 514/248 |
| 5,322,844 A | | 6/1994 | Aranda et al. |
| 5,387,584 A | | 2/1995 | Schnur |
| 5,595,756 A | * | 1/1997 | Bally et al. ................. 424/450 |
| 5,602,184 A | | 2/1997 | Myers et al. |
| 5,626,854 A | | 5/1997 | Ichii et al. |
| 5,795,910 A | | 8/1998 | Giese et al. |
| 5,830,887 A | | 11/1998 | Kelly |
| 5,911,995 A | | 6/1999 | Uckun |
| 6,028,061 A | * | 2/2000 | Bernfield et al. ............. 514/54 |
| 6,147,107 A | | 11/2000 | Dent et al. |
| 6,268,163 B1 | | 7/2001 | Kongsbak et al. |

FOREIGN PATENT DOCUMENTS

| | | |
|---|---|---|
| DE | 3829200 | 1/1990 |
| EP | 0 448 029 A2 | 3/1991 |
| FR | 2 706 771 | 12/1994 |
| GB | 2 151 924 | 7/1985 |
| GB | 2 151 924 A | 7/1985 |
| WO | WO 93/09770 | 5/1993 |
| WO | WO 98/48790 | 11/1998 |

OTHER PUBLICATIONS

Gura, T. Systems for Identifying new Drugs are Often Faulty; Science, vol. 278, 1997, pp. 1041-1042.*

Saeed et al. EUGENOL: a Dual Inhibitor of Platelet-Activating Factor and Arachidonic Acid Metabolism; Phytomedicine (1995), 2 (1), 23-28, 2 page CAPLUS Abstract provided.*

Clardiello et al. Interactions Between the Epidermal Growth Factor Receptor and Type I Protein Kinase A: Biological Significance and Therapeutic Implications; Clinical Cancer Research vol. 4, pp. 821-828.*

Yokota et al. Suppressed Mutagenicity of Benzo[a]pyrene by the Liver S9 Fraction and Microsomes from Eugenol Treated Rats; Mutation Research, 172 pp. 231-236.*

(Continued)

*Primary Examiner*—Patricia Leith
(74) *Attorney, Agent, or Firm*—Nixon & Vanderhye P.C.

(57) ABSTRACT

Pharmaceutical compositions containing plant essential oil compounds, natural or synthetic, or mixtures or derivatives thereof, with one or more signal transduction modulators, for the prevention and treatment of cancer.

3 Claims, 5 Drawing Sheets

OTHER PUBLICATIONS

Azuine, M.A. et al., "Chemopreventive efficacy of betal leaf extract and its constituents on 7,12-dimethylbenz(a) anthracene induced carcinogenesis and their effect on drug detoxification sustem in mouse skin", *Indian Journal of Experimental Biology*, 29(4);346-351 (1991).

Baker, P.R. et al., "Cell signaling and basement membrane degradation by breast cancer cells", *British Journal of Cancer*, 69(Suppl. 21): 18 (1994).

Kinoshita, E. et al., "Activation of MAP kinase cascade induced by human pancreatic phospholipase $A_2$ in a human pancreatic cancer cell line", *FEBS Letters*, 407(3):343-346 (1997).

Nayfield, S.G., "Tamoxifen's role in chemoprevention of breast cancer: an update", *Journal of Cellular Biochemistry*, Suppl. 22:42-50 (1995).

Strobl, J.S. et al., "Mitogenic signal transduction in human breast cancer cells", *General Pharmacology*, 26(8):1643-1649.

Tzanakakis, G.N. et al., "Inhibition of hepatic metastasis from a human pancreatic adenocarcinoma (RWP-2) in the nude mouse by prostacyclin, forskolin, and ketoconazole", *Cancer*, 65(3):446-451 (1990).

Yokota, H. et al., "Enhancement of UDP-glucuronyltransferase, UDP-glucose dehydrogenase, and glutathione S-transferase activities in rat liver by dietary administration of eugenol", *Biochemical Pharmacology*, 37(5):799-802 (1988).

Bardon, S. et al., "Monoterpenes Inhibit Cell Growth, Cell Cycle Progression, and Cyclin D1 Gene Expression in Human Breast Cancer Cell Lines", *Nutrition and Cancer*, 32(1):1-7 (1998).

Berthois, Y. et al., "Phenol Red in Tissue Cculture Media is a Weak Estrogen: Implications Concerning the Study of Eestrogen-Responsive Cells in Culture", *Proc. Natl. Acad. Sci.*, 83:2496-2500 (Apr. 1986).

Ciardiello, F. et al., "Interactions between the Epidermal Growth Factor Receptor and Type I Protein Kinase A: Biological Significance and Therapeutic Implications", *Clinical Cancer Research*, 4:821-828 (Apr. 1998).

Davis, D. et al, "Medical Hypothesis: Xenoestrogens As Preventable Causes of Breast Cancer", *Env. Health Per.*, 101(5):372-377 (Oct. 1993).

Dees, C. et al., "Dietary Estrogens Stimulate Human Breast Cells to Enter the Cell Cycle", *Environ. Health Perspect.*, 105(Suppl 3):633-636 (Apr. 1997).

Dewailly, E. et al., "High Organochlorine Body Burden in Women With Estrogen Receptor-Positive Breast Cancer", *J. Nati. Cancer Inst.*, 86(3):232-234.

Gura, T., "Systems for Identifying New Drugs Are Often Faulty", *Science*, 278:1041-1042 (Nov. 1997).

Harris, J. et al., "Breast Cancer", *New England J. of Med.*, 327(5):319-318 (1992).

Henderson, B. et al., "Hormonal Chemoprevention of Cancer in Women", *Science*, 259:633-638 (1993).

Hoffman, M., "New Clue Found to Oncogene's Role in Breast Cancer", *Science*, 256:1129 (1992).

Jobling, S. et al., "A Variety of Environmental Persistent Chemicals, Including Some Phthalate Plasticizers, Are Weakly Estrogenic", *Envir. Health. Per.*, 103:582-587 (1995).

Kim et al., "Antiananphylactic Properties of Eugenol", *Pharma. Res.*, 36(6):475-480 (1997).

Miller, F. et al., "Xenograft Model of Progressive Human Proliferative Breast Disease", *J. Natl. Cancer Inst.*, 85(21): 1725-1731 (1993).

Mussalo-Rauhamaa, H. et al., "Occurrence of Beta-Hexachlorocyclohexane in Breast Cancer Patients", *Cancer*, 66:2124-2128 (1990).

Nelson, J. et al., "Estrogenic Activities of Chlorinated Hydrocarbons", *J. Tox. Envir. Health*, 4:325-339 (1978).

Oita et al., "Opthalmic Pharmaceutical", CAPLUS 427328, Patent No. RO84026 (1985) ABSTRACT.

Osborne, C. K. et al., "Antagonism between Epidermal Growth Factor and Phorbol Ester Tumor Promoters in Human Breast Cancer Cells", *J. Clin. Invest.*, 67:943-951 (1981).

Reese, J., et al., "Differential DNA-Binding Abilities of Estrogen Receptor Occupied With Two Classes of Antiestrogens: Studies Using Human Estrogen Receptor Overexpressed in Mammalian Cells", *Nucleic Acids Res.*, 19(23):6595-6602.

Saeed et al., Eugenol: A Dual Inhibitor of Platelet-Activating Factor and Arachidonic Acid Metabolism: *Phytomedicine*, 2(1):23-28 (1995).

Soto, A. M. et al., "The Role of Estrogens on the Proliferation of Human Breast Tumor Cells (MCF-7)", *J. Steroid Biochem.*, 23(1):87-94 (1985).

Sukumaran et al., "Inhibition of Tumour Promotion in Mice by Eugenol", *Indian J. Physiol. Pharmacol.*, 38(4):306-308.

Wolff, M. et al., "Blood Levels of Organochlorine Residues and Risk of Breast Cancer", *J. Natl. Cancer Inst.*, 85(8): 648-652 (1993).

Yokota, H. et al., "Suppressed Mutagenicity of Benzo[α] pyrene by the Liver S9 Fraction and Microsomes from Eugenol-Treated Rats", *Mutation Research*, 172:231-236 (1986).

Sylvie Bardon, et al., Monoterpenes Inhibit Cell Growth, Cell Cycle Progression, and Cyclin D1 Gene Expression in Human Breast Cancer Cell Lines, Nutrition and Cancer, vol. 32, No. 1, 1998, pp. 1-7.

* cited by examiner

CANCER TREATMENT COMPOSITION AND METHOD USING NATURAL PLANT ESSENTIAL OILS WITH SIGNAL TRANSDUCTION MODULATORS

CROSS REFERENCE TO RELATED APPLICATION

This application is a divisional of application Ser. No. 09/455,543, filed Dec. 7, 1999 Now ABN, which claims the benefit of U.S. Provisional Patent Application No. 60/111,271, filed Dec. 7, 1998, the entire disclosures of which are incorporated herein by reference.

FIELD OF THE INVENTION

The present invention relates, in general, to therapeutically effective pharmaceutical compositions containing plant essential oil compounds, with one or more signal transduction modulators and methods for using same for prophylactically or therapeutically treating soft tissue cancer in mammals, including humans, such as, for example, breast cancer.

BACKGROUND OF THE INVENTION

Breast cancer is a proliferative disease of mammary epithelial cells and estrogen has been shown to stimulate cell proliferation of these cells both in culture and in mice (Soto and Sonnenschein, 1985; Osborne, 1981). Xenoestrogens have been proposed to stimulate cell proliferation through binding and activating estrogen receptors (ERs) (Miller et al., 1993; Hoffman, 1992). The incidence of breast cancer has been steadily rising during the past two or three decades, a trend characterized by increasing rates among estrogen-responsive tumors, by continuing increases among older women, and by growing numbers in both developed and developing countries (Harris et al., 1992). Between 1973–1980, the incidence of breast cancer in the United States increased a modest 8% among women under 50 years of age, while it rose 32.1% among women in the age group of 50 years or older (Reese et al., 1991). This upward shift is consistent with the historical pattern of accumulation of organochlorine insecticides residues (xenoestrogens) in the environment (Mussalo-Rauhamaa et al., 1990; Wolff et al., 1993; Davis et al., 1993). Breast cancer is also the second leading cause of cancer deaths in women and it is estimated that in 1998, there will be an additional 43,900 deaths due to breast cancer. Environmental estrogens or endocrine disruptors have been suggested to play a role in the etiology or promotion of breast cancer (Davis et al., 1993; Dewailly et al., 1994). Experimental evidence reveals that xenoestrogens affect estrogen production and metabolism and are among the risk factors that cause breast cancer (Nelson, 1978; Berthois et al., 1986; Henderson et al., 1993; Jobling et al., 1995; Dees et al., 1997). Most of the known risk factors for breast cancer, which at least account for 30% of cases (Henderson et al., 1993) are linked with total life-time exposure to reproductive chemicals such as estrogen and xenoestrogens.

It appears evident that soft tissue cancer in mammals is increasing every year as a result of increased estrogen levels and increased exposure to environmental xenoestrogens. For example, the number of prescriptions of estrogen for women in menopause is rapidly increasing, presently estimated at 50,000,000 prescriptions annually in the United States alone. This increasing use of estrogen partially accounts for the higher risk of breast cancer in both young and middle-aged women. Estrogen is present in all mammals and is essential in women for reproductive organs such as ovary, uterus, breast, etc. In men, however, estrogen is required for sperm production and maturation. The abusive use of estrogen prescribed for women is at least partially responsible for the development of soft tissue cancers, especially breast cancer. It is therefore desirable to antagonize or counteract the adverse effects of estrogen in women.

The current FDA-approved treatments, e.g., tamoxifen, in the United States are effective to some extent in some of the female population in antagonizing the adverse effects of estrogen. Unfortunately, these treatments are not totally effective and may themselves cause additional health related effects, such as uterine cancer. Thus, if one could identify compounds that would make the current treatments more effective, or would work in conjunction with, or in lieu of, the present treatments, it is possible some of these adverse side effects would be alleviated or even eliminated. A possible source of alternative treatments are natural, non-toxic compounds. It is proposed that these compounds would advantageously provide for safer and more effective treatments.

The current literature suggests the use of certain signal transduction modulators as treatments for breast and colon cancer. The use of certain monoterpenoid plant essential oils (alpha-terpineol, linalool, and limonene) is also suggested as a potential treatment for breast cancer. These monoterpenoids however are not totally effective and have been proven to be weak anti-proliferative cancer products. In addition, these data do not suggest the capability of these compounds to antagonize the action of estrogen. This may raise the question of how this product may interact in women with estrogen supplement. None of the data disclose the combination of plant essential oils with signal transduction modulators to enhance the anti-proliferative and anti-estrogenic action of the plant essential oils without additional safety concerns.

Accordingly, there is a great need for novel pharmaceuticals that may be effectively and safely used in the prevention or treatment of soft tissue cancers in mammals.

SUMMARY OF THE INVENTION

An object of the present invention is to provide novel compositions that contain certain plant essential oil compounds, natural or synthetic, or mixtures or derivatives thereof, with one or more signal transduction modulators, as prophylactic for, and treatment of, soft tissue cancer.

The above and other objects are accomplished by the present invention which is directed to novel pharmaceutical compositions containing plant essential oils, including mixtures or derivatives thereof, which are synthetically made or obtained from natural sources, containing signal transduction modulators. In particular, the present invention is directed to a pharmaceutical composition for the prevention or treatment of soft tissue cancer in mammals, comprising a pharmaceutically effective amount of at least one plant essential oil compound and at least one signal transduction modulator in admixture with a pharmaceutically acceptable carrier. The present invention is also directed to methods for using such novel pharmaceutical compositions for prophylactically or therapeutically treating soft tissue cancers.

Additional objects and attendant advantages of the present invention will be set forth, in part, in the description that follows, or may be learned from practicing or using the present invention. The objects and advantages may be realized and attained by means of the features and combinations particularly recited in the appended claims. It is to be understood that the foregoing general description and the following detailed description are exemplary and explanatory only and are not to be viewed as being restrictive of the invention, as claimed.

BRIEF DESCRIPTION OF THE DRAWINGS

The features and advantages of the present invention will become more clearly appreciated from the following description taken in conjunction with the accompanying drawings in which like elements are denoted by like reference numerals.

DETAILED DESCRIPTION OF PREFERRED EMBODIMENTS

Figure 1:
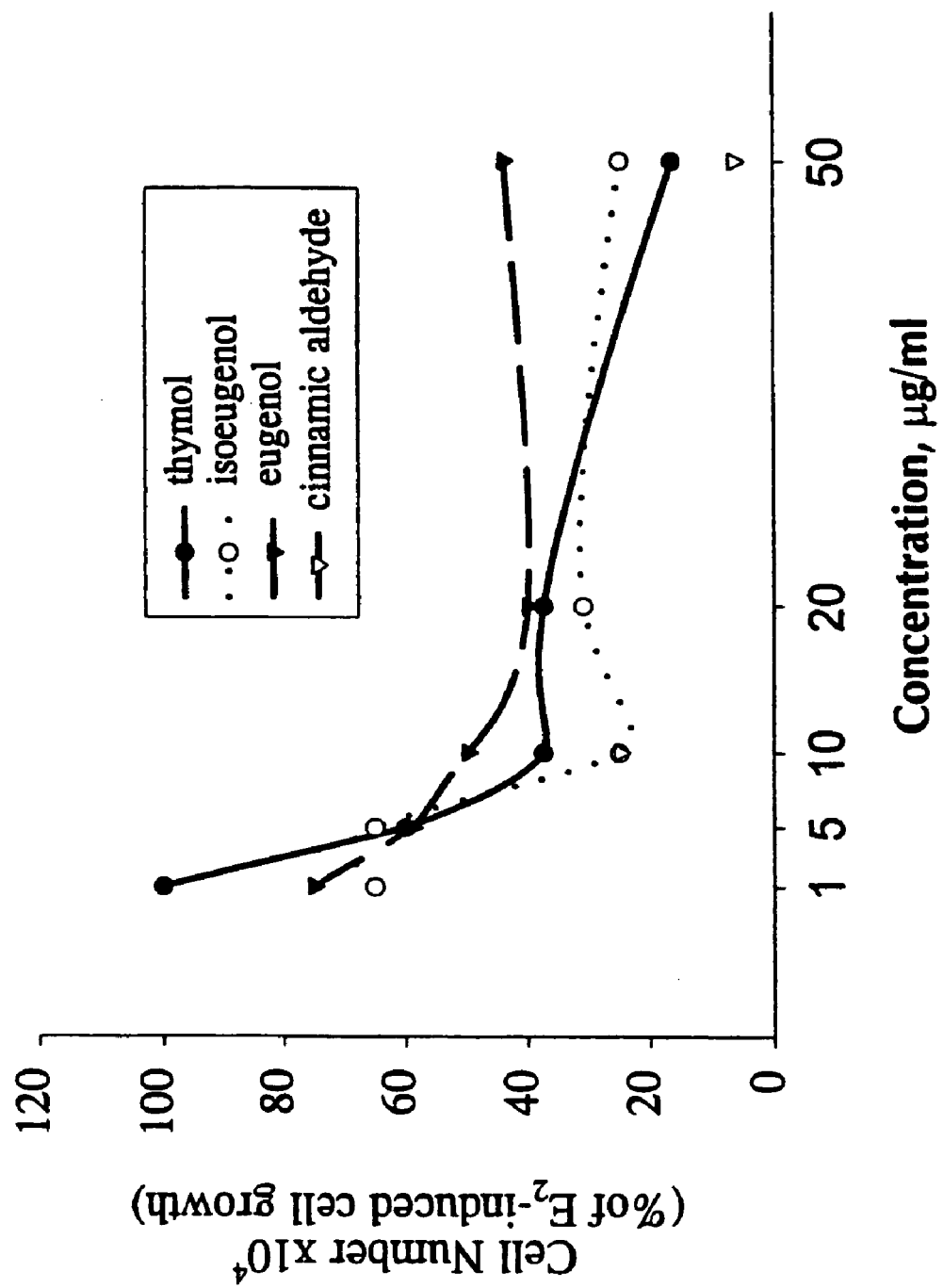
FIG. 1 shows the concentration-response of plant essential oil compounds against $E_2$-induced growth in breast cancer cells.

All patents, patent applications and literatures cited in this description are incorporated herein by reference in their entirety. In the case of inconsistencies, the present disclosure, including definitions, will prevail.

In a preferred embodiment, the present invention provides a novel pharmaceutical composition comprising at least one plant essential oil compound derived from either natural or synthetic sources and at least one signal transduction modulator including mixtures or derivatives of plant essential oil compound.

The specific plant essential oils disclosed herein or derivative thereof comprise a monocyclic, carbocyclic ring structure having six-members and substituted by at least one oxygenated or hydroxyl functional moiety. Non-limiting examples of plant essential oils encompassed within the present invention include members selected from the group consisting of aldehyde C16 (pure), alpha-terpineol, amyl cinnamic aldehyde, amyl salicylate, anisic aldehyde, benzyl alcohol, benzyl acetate, cinnamaldehyde, cinnamic alcohol, α-terpineol, carvacrol, carveol, citral, citronellal, citronellol, p-cymene, diethyl phthalate, dimethyl salicylate, dipropylene glycol, eucalyptol (cineole), eugenol, isoeugenol, galaxolide, geraniol, guaiacol, ionone, d-limonene, menthol, methyl anthranilate, methyl ionone, methyl salicylate, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like. As these plant essential oil compounds are known and used for a variety of other purposes, they may be prepared by a skilled artisan by employing known methods.

The above plant essential oil compounds can also be administered in combination with at least one signal transduction modulator. Non-limiting examples of signal transduction modulators include members selected from the group consisting of cyclic adenosine monophosphate (cAMP)/cAMP-dependent protein kinase, tyrosine kinase, calcium phospholipid-dependent protein kinase (PKC), mitogen activated protein kinase family members, calcium-calmodulin-dependent protein kinase, and growth factor receptor inhibitors. Specific non-limiting examples of such signal transduction modulators include octopamine, forskolin, PD98059, geldanamycin and genistein, and staurosporin. When the plant essential oil compounds of the present invention are administered in combination therapies with other agents, they may be administered sequentially or concurrently to a patient in need of treatment.

The above plant essential oil compounds and signal transduction modulators of the present invention may be purchased from conventional sources, may be readily isolated from specific plants or trees and purified (isolated) or may be synthesized using conventional techniques. Advantageously, these compounds may be conveniently synthesized from readily available starting materials. The relative ease with which the compositions of the present invention can be synthesized represents an enormous advantage in the large-scale production of these compounds.

It will be appreciated that the therapeutically-active plant essential oil compounds of the present invention may be modified or derivatized by appending appropriate functionalities, i.e., functional groups, to enhance selective biological properties. Such modifications are known in the art and include those that increase biological penetration into a given biological compartment (e.g., blood, lymphatic system, central nervous system), increase oral availability, increase solubility to allow administration by injection, alter metabolism and alter rate of excretion. In addition, the plant essential oil compounds may be altered to pro-drug form such that the desired therapeutically-active form of the compound is created in the body of the patient as the result of the action of metabolic or other biochemical processes on the pro-drug. Some examples of pro-drug forms include ketal, acetal, oxime, and hydrazone forms of compounds which contain ketone or aldehyde groups.

Moreover, the therapeutically-effective plant essential oil compounds or derivatives thereof of the present invention may contain one or more asymmetric carbon atoms and thus may occur as racemates and racemic mixtures, single enantiomers, diastereomeric mixtures and individual diastereomers. Each stereogenic carbon may be of the R or S configuration. All such isomeric forms of these compounds are expressly included within the purview of the present invention.

As will be appreciated, the compositions and method of the present invention include pharmaceutical compositions that comprise at least one plant essential oil, and pharmaceutically acceptable salts thereof, in combination with any pharmaceutically acceptable carrier, adjuvant or vehicle. The term "pharmaceutically acceptable carrier or adjuvant" refers to a carrier or adjuvant that may be administered to a patient, together with a plant essential oil compound of the present invention, and which does not destroy the pharmacological activity thereof and is nontoxic when administered in doses sufficient to deliver a therapeutic amount of the compound.

Pharmaceutically acceptable salts of the plant essential oil compounds of this invention include those derived from pharmaceutically acceptable inorganic and organic acids and bases. Examples of suitable acid salts include, without limitation, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N-($C_{1-4}$ alkyl)4+ salts. The present invention also envisions the quaternization of any basic nitrogen-containing groups of the compounds disclosed herein. Water or oil-soluble or dispersible products may be obtained by such quaternization.

Further, pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d.alpha-tocopherol polyethyleneglycol 1000 succinate, or other similar polymeric delivery matrices or systems, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-.beta.-cyclodextrins, or other solublized derivatives may also be advantageously used to enhance delivery of therapeutically-effective plant essential oil compounds and signal transduction modulators of the present invention.

The pharmaceutical compositions of this invention may be administered orally, parenterally, by inhalation spray, topically, rectally, nasally, buccally, vaginally or via an implanted reservoir, however, oral administration or administration by injection is preferred. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of the present invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of the present invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Although rare, topical administration of the pharmaceutical compositions of the present invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in-a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Another acceptable pharmaceutical preparation would be an encapsulated form of the plant essential oils, as is, or modified as per the prior descriptions. The walls of the capsules could be designed to release the plant essential oils rapidly, i.e. one minute, hour or day, or it could be designed to release over some designated period of time, i.e. days, weeks or months. The wall materials could be natural or synthetic polymers acceptable to the US FDA or composed of lipids or other suitable materials. These capsules could be delivered either orally or by injection and could be either water or oil based depending upon the desired method of use or required rate of release.

Dosage levels of between about 0.001 and about 100 mg/kg body weight per day, preferably between about 0.5 and about 75 mg/kg body weight per day of the active ingredient compound are useful in the prevention and treatment of soft tissue cancers. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

The prophylactic use of the present invention may require the daily intake of a prophylactically-effective amount.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of a cancer, the patient's disposition to cancer and the judgment of the treating physician.

The compositions and methods of the present invention will be further illustrated in the following, non-limiting Examples. The Examples are illustrative of various embodiments only and do not limit the claimed invention regarding the materials, conditions, weight ratios, process parameters and the like recited herein. The Examples show, inter alia, that certain signal transduction modulators synergize the anti-estrogenic activity of plant essential oil compounds against estrogen ($E_2$)-induced abnormal cell growth in human epithelial breast cancer cells. When reading the following Examples, it will be appreciated that the growth and proliferation of MCF-7 cells are strictly estrogen-dependent. In the presence of estrogen, the cells grow, confluent and form foci, the landmark of tumor diagnosis. In the absence of estrogen, the growth of these cells is slow and the formation of foci is rare.

EXAMPLE 1

Various concentrations of plant essential oil compounds were tested against $E_2$-induced cell growth to determine the lowest concentrations that antagonize the $E_2$-induced cell growth. MCF-7 cells were cultured in growth medium supplemented with 10% fetal bovine serum (FBS). At 85% confluence, cells were sub-cultured in 6 well petri-dishes and supplemented with 5% FBS serum stripped medium, phenol red free for 24 hours prior to the treatment of different concentrations of the test chemicals. After 5 days of treatment cells were trypsinized and collected using an Eppendorf microcentrifuge. The cell pellets were resuspended in 1% trypan blue. Three aliquots (10 ul each) of the viable cell suspension was counted using a haemocytometer assay. Each sample was then counted three times and to obtain an average count. The compounds were tested in the presence of 10 nM estrogen (=2.7 ng estrogen/ml). Two wells per test concentration were used. This experiment was repeated two times. A control sample-received solvent only at <0.1% ethanol.

FIG. 1 shows that there is a dose-response dependent relationship between plant essential oil compounds and their antiestrogenicity against $E_2$-induced abnormal cell growth in human epithelial breast cancer cells (MCF-7). The data demonstrates that thymol at low dose (5 ug/ml) provided 40% protection against the $E_2$-induced cell proliferation. In addition, eugenol (1 ug/ml) and isoeugenol (1 ug/ml) provide 35% and 25% protection, respectively, against $E_2$-induced abnormal cell growth. Cinnamic aldehyde (10 $\mu$g/ml) and isoeugenol both expressed approximately 75% protection against the $E_2$-induced abnormal cell growth.

EXAMPLE 2

Figure 2:
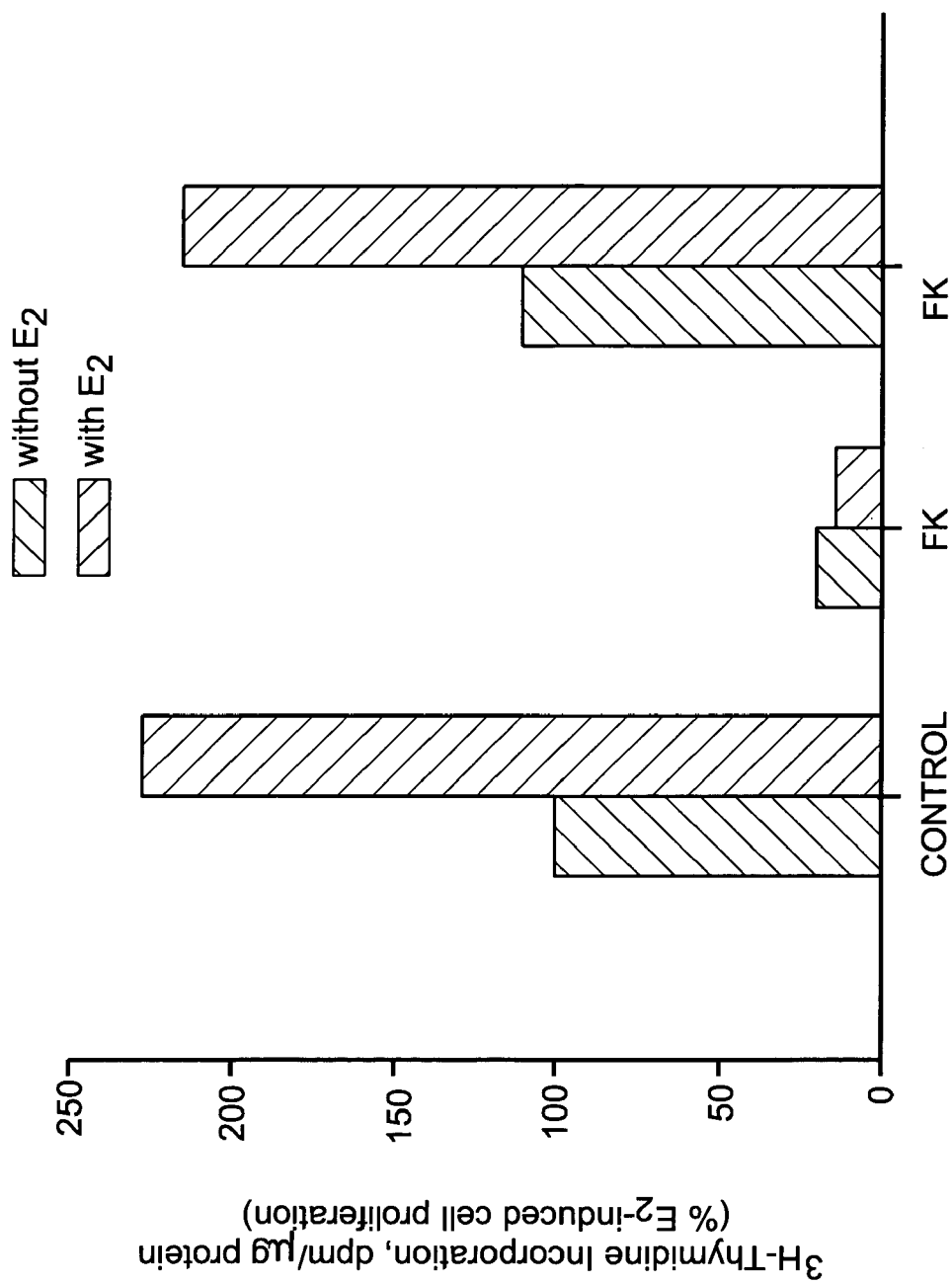
FIG. 2 shows the effect of cAMP inducer, forskolin (FK), and c-Src kinase inhibitor, geldanamycin (GM) on $E_2$-induced proliferation in breast cancer cells.
Figure 3:
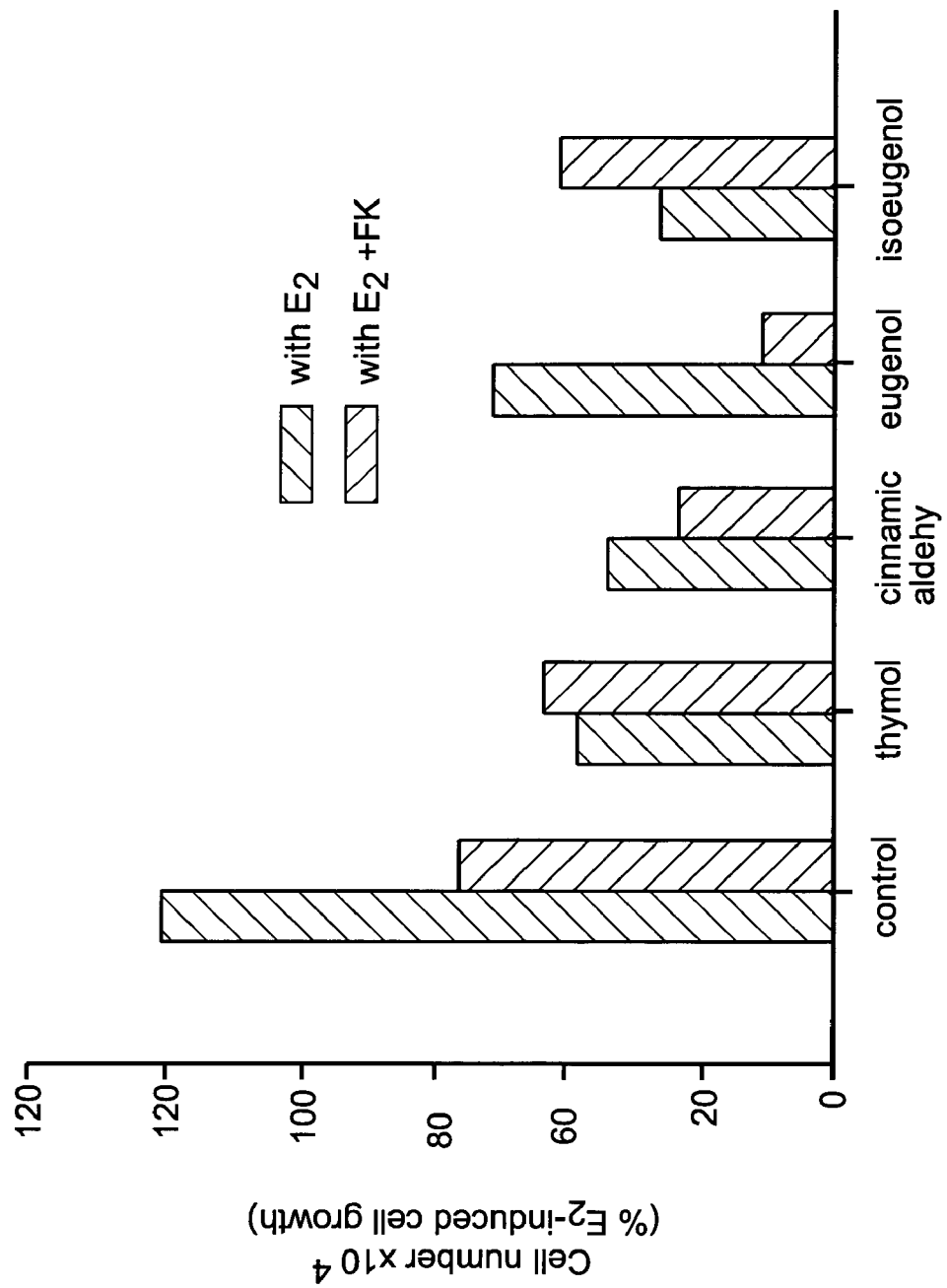
FIG. 3 shows the effect of mixed exposure of plant essential oil compounds and cAMP inducer forskolin (FK) on $E_2$-induced breast cancer cell growth.
Figure 4:
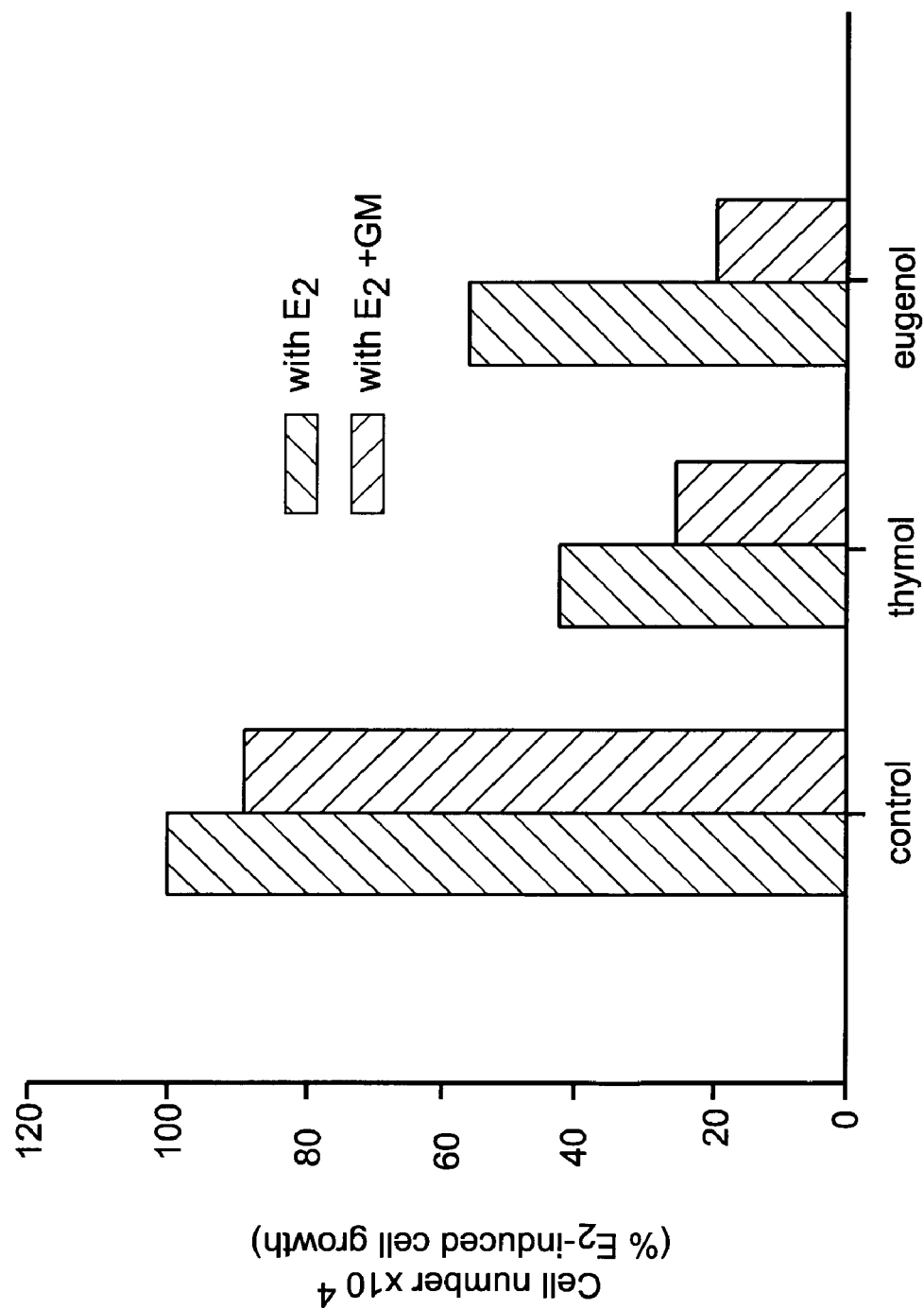
FIG. 4 shows the effect of c-Src kinase inhibitor, geldanamycin (GM) on the antiestrogenic activity of plant essential oil compounds against $E_2$-induced growth in breast cancer cells.

This Example shows the mixed exposure effect of plant essential oil compounds and signal transduction modulators, particularly, cAMP/PKA activator (forskolin, FK) and tyrosine kinase family member, c-Src kinase ($p^{scr60}$), inhibitor, geldananmycin on $E_2$-induced cell growth. MCF-7 cells were cultured in growth medium supplemented with 10% fetal bovine serum (FBS). At 85% confluence, cells were sub-cultured in 6 well petri-dishes medium supplemented with 5% FBS serum stripped medium, phenol red free for 24 hours prior to the treatment of different concentrations of the test chemicals. Cells were either counted (5 days after treatment) or used to determine cell proliferation (24 hr after treatment) using $^3$H-thymidine incorporation. To count the cell, cells were trypsinized, and collected using Eppendorf microcentrifuge. The cell pellets were resuspended in 1% trypan blue and three aliquots (10 ul each) of the viable cell suspension was counted using a haemocytometer assay. Each sample was then counted three times to obtain an average count. For thymidine incoroporation, 24 hr after cell treated with test mixture, cells were incubated with 1 uCi $^3$H-thymidine. After 2 hr, the medium was withdrawn and the cells were washed with thymidine-free medium and 10% TCA prior to radioactive count. Plant essential oil compounds were tested in the presence of 10 nM estrogen (=2.7 ng estrogen/ml) using three wells per test concentration. This experiment was repeated two times. A control sample received solvent only at <0.1% ethanol. Results are shown in FIGS. 2–4. The data supports the involvement of cellular signaling proteins, particularly cAMP/PKA cascade in the $E_2$-induced cell proliferation in human breast cancer cells as judged by the antiestrogenic activity of FK. However, different methods are required to evaluate antiestrogenic activity.

FIG. 2 shows that cAMP inducer is capable of blocking cancer cell proliferation regardless of whether the cell growth or cell proliferation is estrogen receptor (ER)-dependent or ER-independent as judged by the action of FK 5 $\mu$M (=2.05 $\mu$g/ml) in the presence and absence of $E_2$. The data in FIG. 2, however, suggests that c-Src kinase is not a factor in $E_2$-induced abnormal cell proliferation because GM did not antagonize $E_2$-induced incorporation of $^3$H-thymidine, which is the biomarker for DNA replication.

FIG. 3 demonstrates the interaction of FK with certain plant essential oil compounds. FK does not appear to act as a synergist for all of the tested plant essential oil compounds. For instance, the data shows that FK synergizes the antiestrogenic activity of eugenol and cinnamic aldehyde, but not thymol or isoeugenol, which suggests that chemical structure is important to the synergistic activity of FK against cell proliferation.

FIG. 4 shows the involvement of a tyrosine kinase family member, c-Src kinase, in the growth of breast cancer cells. GM (10 ng/ml), the c-Src kinase inhibitor, potentiates the antiestrogenic activity of $E_2$-on cell growth. GM also synergizes the antiestrogenic activity of eugenol against $E_2$ induced cell growth.

EXAMPLE 3

This Example shows the mixed exposure effect of plant essential oil compounds and signal transduction modulators, serine/threonine phosphatase inhibitor, okadaic acid (OA), on Human Epithelial Breast Cancer Cells (MCF-7). MCF-7 cells were cultured in growth medium supplemented with 10% fetal bovine serum (FBS). At 85% confluence, cells were sub-cultured in 6 well petri-dishes medium supplemented with 5% FBS serum stripped medium, phenol red free for 24 hours prior to the treatment of 10 ug/ml of each plant essential oil compound and 1 nM okadiac acid. After 24 hr treatment, cells were used to determine cell proliferation using $^3$H-thymidine incorporation. Two hrs after cell incubation with 1 uCi $^3$H-thymidine, the medium was withdrawn and the cells were washed with thymidine-free medium and 10% TCA prior to radioactive count. These test chemicals were tested in the presence of 10 nM estrogen (=2.7 ng estrogen/ml). Three wells per test concentration were used. This experiment was repeated two times. A control sample received solvent only at <0.1% ethanol.

Figure 5:
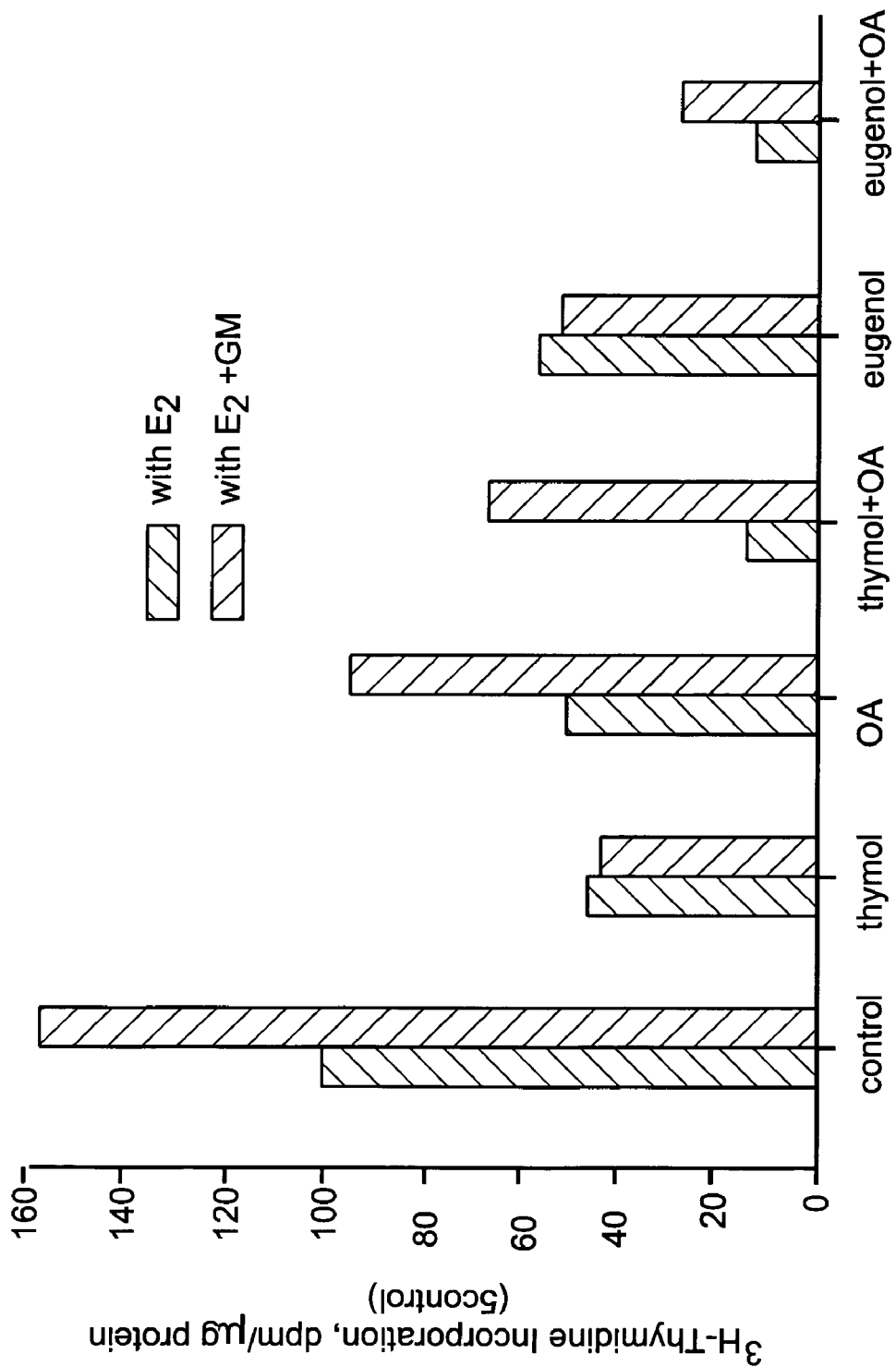
FIG. 5 shows the mixed exposure effect of okadaic acid (OA) (a serine/threonine protein phosphatase inhibitor) and plant essential oil compounds on the growth of breast cancer cells in the presence and absence of $E_2$.

FIG. 5 shows that protein phosphatase(s) is involved in the biological activity of $E_2$. The action of OA is highly expressed in the absence of $E_2$. For example OA synergies the antiestrogenic activity of thymol only in the absence of $E_2$. On the other hand, OA synergies the antiestrogenic action of eugenol regardless of the absence or presence of $E_2$.

The above Examples show, inter alia, that one or more signal transduction modulators may be used in combination with plant essential oil compounds and derivatives thereof to provide anti-proliferative, anti-estrogenic and/or anti-mitogenic compositions for prophylactically and/or therapeutically treating soft tissue cancers.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for treating breast cancer comprising:
   administering to a patient in need thereof a therapeutically effective amount of a composition comprising: a pharmaceutically acceptable carrier and a pharmaceutically effective amount of an active ingredient comprising eugenol and forskolin.

2. A method for inhibiting the growth of breast cancer cells comprising applying to a population of the breast cancer cells, for a sufficient time to observe inhibition of growth in said breast cancer cells, an effective amount of a composition comprising eugenol and forskolin.

3. The method of claim 2, wherein the breast cancer cells are MCF-7 cells.

* * * * *